(12) United States Patent
Zeitels (10) Patent No.: US 6,955,645 B1
(45) Date of Patent: Oct. 18, 2005

(54) UNIVERSAL MODULAR GLOTTISCOPE SYSTEM HAVING INTRA-WALL CHANNELS FOR VOCAL FOLD MICROSURGERY OR OROTRACHEAL INTUBATION

(76) Inventor: Steven M. Zeitels, 166 Beacon St., #3, Boston, MA (US) 02116

(*) Notice: Subject to any disclaimer, the term of this patent is extended or adjusted under 35 U.S.C. 154(b) by 0 days.

(21) Appl. No.: 10/061,256

(22) Filed: Feb. 4, 2002

Related U.S. Application Data (63) Continuation-in-part of application No. 09/548,357, filed on Apr. 12, 2000, now abandoned.
(60) Provisional application No. 60/128,793, filed on Apr. 12, 1999.

(51) Int. Cl.$^7$ .............................................. A61B 1/267
(52) U.S. Cl. ..................... 600/187; 600/190; 600/194; 600/199
(58) Field of Search ................................ 600/185, 187, 600/188, 190, 193, 197, 235, 237, 194, 199, 600/205, 201, 208

(56) References Cited

U.S. PATENT DOCUMENTS

| | | | | |
|---|---|---|---|---|
| 4,306,547 A | * | 12/1981 | Lowell | 600/188 |
| 4,384,570 A | * | 5/1983 | Roberts | 600/187 |
| 4,527,553 A | * | 7/1985 | Upsher | 600/188 |
| 4,567,882 A | * | 2/1986 | Heller | 600/249 |
| RE32,158 E | * | 5/1986 | Vukovic | 600/123 |
| 4,947,829 A | * | 8/1990 | Bullard | 600/101 |
| 4,947,896 A | * | 8/1990 | Bartlett | 600/187 |
| 4,982,729 A | * | 1/1991 | Wu | 600/187 |
| 5,261,392 A | * | 11/1993 | Wu | 600/188 |
| 5,287,848 A | * | 2/1994 | Cubb et al. | 128/200.26 |
| 5,758,456 A | * | 6/1998 | Case | 52/177 |
| 5,800,344 A | * | 9/1998 | Wood et al. | 600/188 |
| 5,817,005 A | * | 10/1998 | Cohen | 600/201 |
| 5,893,830 A | * | 4/1999 | Zeitels | 600/190 |
| 5,944,654 A | * | 8/1999 | Crawford | 600/157 |
| 6,080,102 A | * | 6/2000 | Konou et al. | 600/114 |
| 6,629,924 B2 | * | 10/2003 | Aydelotte | 600/120 |
| 2002/0022769 A1 | * | 2/2002 | Smith et al. | 600/188 |
| 2002/0144340 A1 | * | 10/2002 | Last | 4/502 |
| 2003/0150555 A1 | * | 8/2003 | Gandhi et al. | 156/292 |

\* cited by examiner

*Primary Examiner*—John P. Leubecker
(74) *Attorney, Agent, or Firm*—McDermott Will & Emery LLP (57) ABSTRACT

An element for a phonomicrosurgical modular glottiscope system comprises a proximal end; a distal end; a pair of opposing curved sides intersecting at an apex line; a substantially planar base, and internal channels disposed within the base. The base plate is removably attached to the pair of curved sides, and the base and curved sides define a lumen extending from the proximal end to the distal end. The internal channels include a first internal channel that provides illumination to the distal end and a second internal channel that provides aspiration to the distal end. In operation, the distal end of the element is inserted into a body cavity and the lumen provides visualization of the distal end and access to the distal end for tools inserted into the lumen from the proximal end. A method of manufacturing the element is also disclosed.

22 Claims, 9 Drawing Sheets

UNIVERSAL MODULAR GLOTTISCOPE SYSTEM HAVING INTRA-WALL CHANNELS FOR VOCAL FOLD MICROSURGERY OR OROTRACHEAL INTUBATION

CROSS REFERENCE TO RELATED APPLICATIONS

This application is a Continuation-In-Part of application Ser. No. 09/548,357, filed on Apr. 12, 2000, now abandoned, and to Provisional Application Ser. No. 60/128,793, filed on Apr. 12, 1999, both incorporated herein by reference.

FIELD OF THE INVENTION

This invention relates to any rigid endoscope including this glottiscope system which enables a surgeon to perform laryngoscopic surgery, and more particularly, to a novel modular glottiscope system in which carriers are provided within the walls of the glottiscope. This application is related to subject matter contained within U.S. Pat. No. 5,893,830 to Zeitels, the inventor of the present invention, and entitled Universal Modular Laryngoscope/Glottiscope System, which is incorporated herein by reference.

BACKGROUND OF THE INVENTION

Laryngoscopes, also known as glottiscopes, are routinely used to facilitate endotracheal intubation of patients, e.g., to provide a temporary air passage for administration of anesthetic substance or to overcome an obstruction of the air passage to a patient's lungs. Glottiscopes, in various forms, provide the surgeon with access to examine and surgically manipulate the vocal folds and operate to distract the soft tissues of the oral cavity, pharynx and supraglottic larynx. This is a procedure known as direct laryngoscopy.

A typical glottiscope has an elongate element, which may be of variable geometry, that is introduced through the patient's mouth into the larynx. An attached handle enables the surgeon to manipulate not only the element introduced into the patient's larynx but, as appropriate, to position the distal end of the inserted element to perform inspection and/or surgical operations. The glottiscope typically includes a lumen, through which an endotracheal tube or alternatively, one or more surgical tools can be simultaneously inserted. Otolaryngologists typically use a tubular glottiscope, which is inserted into the patient's larynx to the glottis, i.e., the true vocal cords or folds, both for viewing and for endoscopic surgical operations.

The surgeon must have a clear view of the affected tissue and must be able to perform precise surgery, sometimes with more than one tool utilized simultaneously. Because of the limited dimensions of the human oral cavity, pharynx and larynx, it is extremely important to enable the surgeon to have the widest access and maximum freedom for manipulating necessary instrumentation, and to reduce the time during which physical invasion of the patient's larynx must occur.

Particularly for patients who need to improve or maintain their voices, specialized surgery known as phonomicrosurgery is performed with the use of a surgical microscope. Such phonomicrosurgery is optimized by obtaining the widest glottal surgical field to expose vocal-fold anomalies such as polyps, nodules, cysts, granulomas, papilloma, epithelial dysplasia, and cancerous growths.

The human vocal folds (glottis) comprise an approximately isosceles-triangle-shaped valve that is fixed anteriorly and opens and closes posteriorly to respectively allow for respiration and phonation. Lesions of the vocal folds may occur in patients of all ages and of both genders. A clear human voice is predicated on aerodynamically-driven, symmetrically-entrained oscillation of the vocal folds. When the vocal folds are closed during phonation, the expired air stream from the trachea is opposed by the closed glottal valve. Under sustained aerodynamic pressure, the vocal folds will vibrate to generate phonation. If there is a lesion on the vocal folds, this vibration becomes disordered, and hoarseness develops. Most benign lesions of the vocal folds, except lesions caused by viral infection, tend to develop in vocal over-users.

The design goal of any glottiscope is to provide an internal portion, or lumen, that provides the widest internal viewing and working area. This is achieved by minimizing the differential between the inner and outer diameter of the tube and by optimally designing the contours of the tube, as discussed in U.S. Pat. No. 5,893,830 to Zeitels. This allows for the placement and advancement of the largest glottiscope possible through the aforementioned soft tissues. A narrower outer diameter of the tube also allows for easier placement and insertion of the glottiscope.

The placement of any glottiscope requires illumination to facilitate the maneuvering and to avoid unnecessary tissue trauma. In 1895, the first illumination was provided by a headlight, and in the 20th century, light carriers were attached to the laryngoscopes. In present glottiscopes, however, small bulbs, fiber-optics, or polymers that transmit light are typically used to provide illumination. In these present models, problems result from the light carrier widening the outer diameter of glottiscope. A problem with placing the light carrier laterally on the glottiscope is that the light carrier widens the outer diameter of the glottiscope and impairs placement of the glottiscope if the individual has a small mandible.

Another problem can result if the light carrier is situated in part or completely within the lumen of the glottiscope. Any light carrier that commences outside the laryngoscope tube must eventually enter the lumen to provide internal illumination. This leads to partial obstruction of the intralumenal visual/surgical field. Furthermore, the position of the light carrier can inhibit the range of motion of hand instruments and/or preclude the use of a laser in certain locations of the visual/surgical field. The obstruction of the visual/surgical field induced by the light carrier varies by degree but is present in all current models of tubular glottiscopes.

In certain glottiscope models, in which the light carrier remains entirely within the lumen of the laryngoscope tube, the placement of the light carrier leads to even worse obstruction than previously described. The advantage, however, of an internal light carrier is that the outer diameter of the tube is narrower, which facilitates the advancement of the glottiscope past the mandible and the associated soft tissues. The need for a suction aspiration cannula, in addition to the light-carrier, exacerbates even further both problems described above. Accordingly, a need exists for an improved glottiscope design that provides for illumination and suction in which the lumen, and therefore the visual/surgical field, is not obstructed and in which the advancement of the glottiscope is not impaired by an enlarged diameter of the glottiscope.

SUMMARY OF THE INVENTION

This and other needs are met by embodiments of the present invention which provide an element for a surgical system. The element comprises a proximal end, a distal end a lumen, and one or more internal channels disposed within the walls. The walls can include a substantially planar base and a pair of opposing curved sides. The lumen is defined by the walls and extends from the proximal and distal ends of the element. In operation, the distal end of the element is inserted into a body cavity and the lumen provides visualization of the distal end and access to the distal end for tools inserted into the lumen from the proximal end. An advantage of placing the internal channel within the wall surrounding the lumen is that interference by the channel is minimal when the lumen is accessed. The base can also be detachably connected to the curved sides.

A further aspect of the present invention is that the surgical system is a modular glottiscope and includes the base having a first channel for providing illumination and a second channel for providing aspiration. By providing illumination and aspiration, the user of a modular glottiscope is able to illuminate the vocal folds and remove tissue and/or other material from the surgical field. By placing the internal channels within the base, the thickness of the base is enlarged. This enlargement will be least likely to restrict placement and advancement of the glottiscope in a patient with anatomical factors such as narrow mandible, restricted temporo-mandibular joint opening, large tongue base, or a cephalad-positioned larynx.

Another aspect of the present invention is that the base can include a first portion and a second portion, with the first portion having a pair of longitudinally extending slots. Covering the slots in the second portion forms the internal channels that provide a pathway for placing and stabilizing a cannula for illumination and a cannula for aspiration. The cannulae can be respectively inserted into the pair of longitudinally extending channels to provide illumination and aspiration to the distal end of the element.

In another aspect of the invention, the surgical system is a modular glottiscope designed for transoral translaryngeal intubation of the trachea. The longitudinal examining element includes a pair of opposing curved sides forming a lancet-arch shaped spatula/speculum and an internal channel is present for providing illumination to the distal end. The internal channel is disposed at the intersection of the opposing curved sides. The curved sides each include longitudinally extending free ends, which define an opening to a lumen. The arched shape of the curved sides provides a direct path to the glottal aperture and precludes soft tissue of the larynx, pharynx or oral cavity from obscuring visualization and intubation. Unlike the phonomicrosurgical glottiscope in which the channels are optimally placed in the base plate, in the intubation glottiscope, the internal channel is placed at the intersection of the arched sides. This is ideal for intubation because only visualization of the posterior glottis is necessary.

When used as a part of a modular glottiscope system, a plurality of elements of different dimensions are provided. Also, a standardized handle-attachment member is affixed adjacent the proximal end of each of the longitudinal examining speculae. A handle attachable to the standardized handle-attachment member of the elements is also provided. A second handle attachable to the first handle element can be positioned parallel to the examining speculum.

Additional advantages of the present invention will become readily apparent to those skilled in this art from the following detailed description, wherein only the preferred embodiment of the present invention is shown and described, simply by way of illustration of the best mode contemplated for carrying out the present invention. As will be realized, the present invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawing, wherein elements having the same reference numeral designations represent like elements throughout, and wherein.

DETAILED DESCRIPTION OF THE INVENTION

Figure 1:
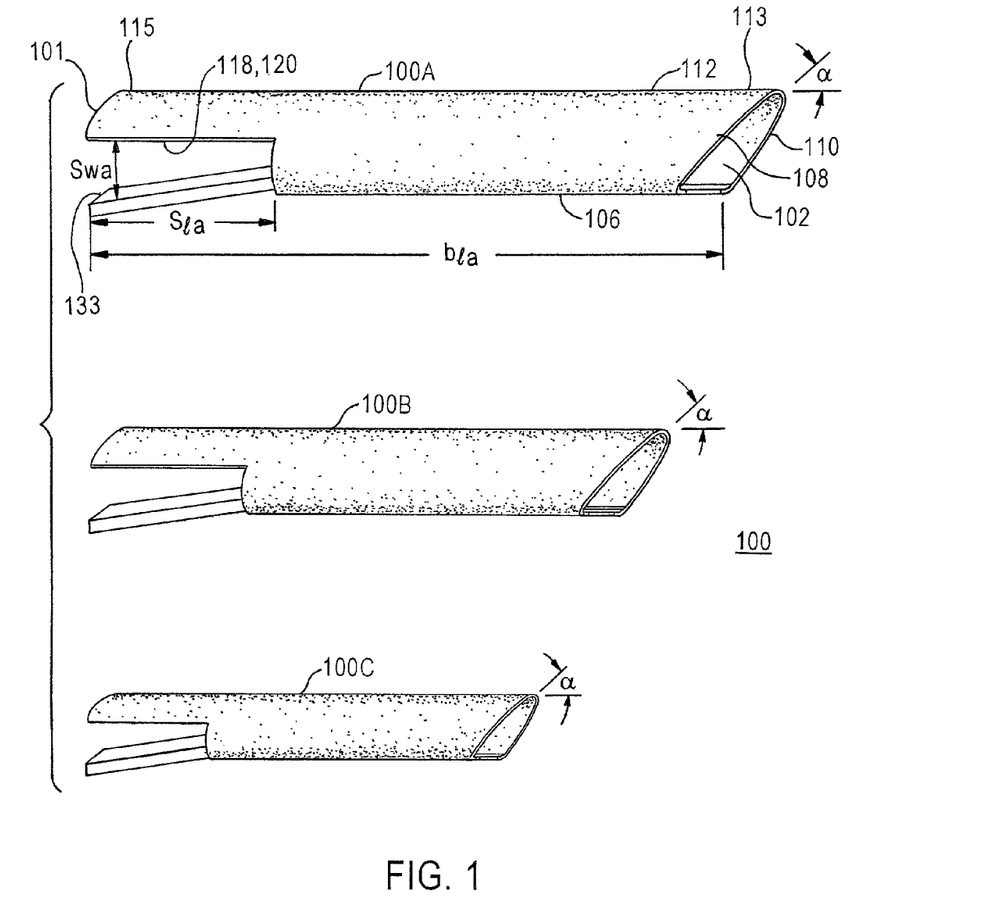
FIG. 1 is a side perspective view of a set of three elements, of different dimensions but otherwise similar geometry, in accordance with the invention.
Figure 2A:
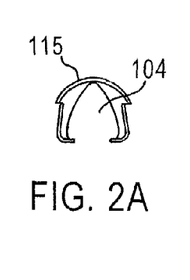
FIGS. 2A–2D respectively show proximal, distal, side and elevated distal views of a first element, in accordance with the invention.
Figure 2B:
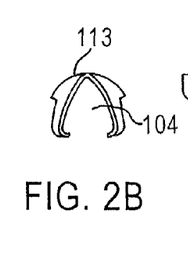
Figure 2C:
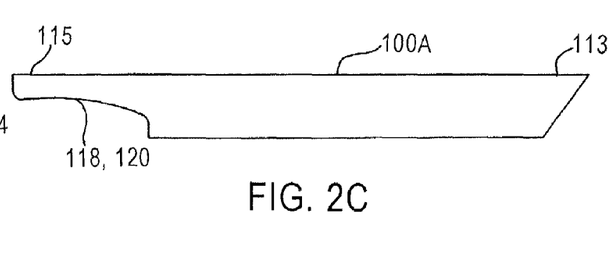
Figure 2D:
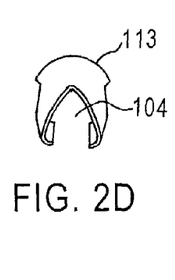
Figure 3A:
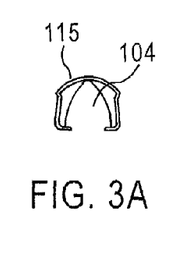
FIGS. 3A–3D respectively show proximal, distal, side and elevated distal views of a second element, in accordance with the invention.
Figure 3B:
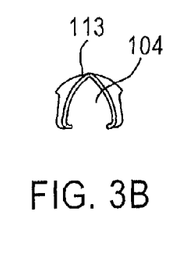
Figure 3C:
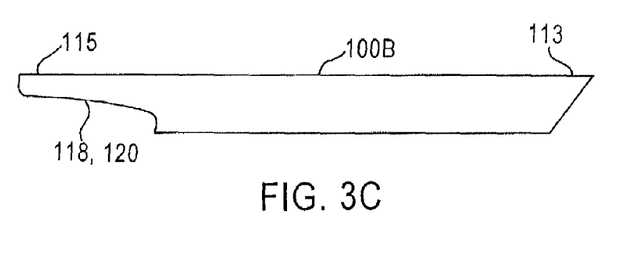
Figure 3D:
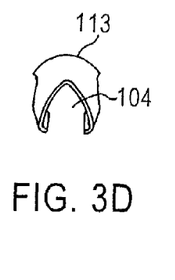
Figure 4A:
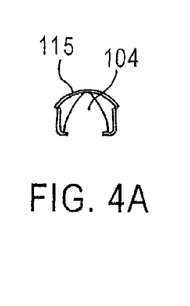
FIGS. 4A–4D respectively show proximal, distal, side and elevated distal views of a third element, in accordance with the invention.
Figure 4B:
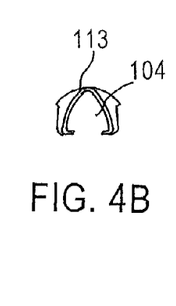
Figure 4C:
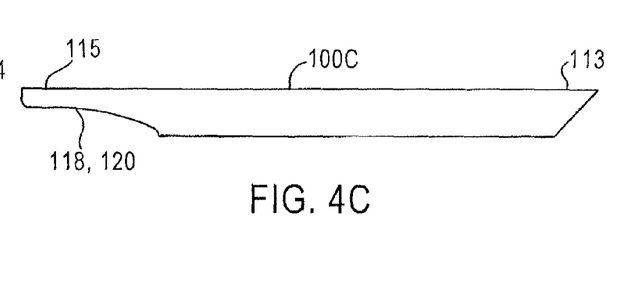
Figure 4D:
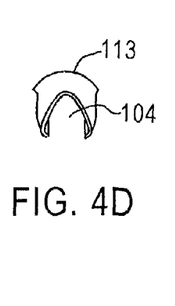

A modular system according to current aspects of the present invention is illustrated in FIG. 1 and comprises a set 100 of elements 100A–C for a surgical system. The elements 100A–C of the set 100 are not limited as to a particular number of elements 100A–C. Also, each element 100A–C is not limited as to a particular function. For example, the elements 100A–C can be used for different instrumentation. One such use is as a spatula for minimally invasive procedures in portions of the body, such as the chest and abdomen.

In a described aspect of the invention, however, the elements 100A–C are used in forming a modular glottiscope system.

Each element 100A–C of the set 100 can be differently dimensioned and interchangeable. For example, consideration can be given to a patient's physical size by the elements 100A–C of the set 100 having similar functions but different dimensions. Thus, when a patient's size dictates, an element 100A–C with the most appropriate dimension can be used in place of another element 100A–C, less appropriately dimensioned. An important advantage of the invention is that it permits modularity and, based on actual measurements and/or the surgeon's experience, allows the surgeon to select the particular element 100A–C, which, for example, during laryngoscopic surgery, will most effectively permit inspection and/or surgical treatment of that patient's glottal tissue. The surgeon can thus easily adjust to differing anatomies of patients, since the set 100 should include elements 100A–C of all the necessary sizes.

As illustrated in FIGS. 1–4, in current aspects of the invention, each element 100A–C preferably comprises a distal end 113, a proximal end 115, and at least one longitudinally extending wall 101. The wall 101 defines a lumen 104 extending from the proximal end 115 to the distal end 113. Thus, each element 100A–C is preferably elongate and hollow, most preferably tubular. In operation, an element 100A–C is inserted into a body cavity and the lumen 104 provides visualization through an opening 103 in the distal end 113 and access to the distal end 113 for tools (best shown in FIG. 7) inserted into the lumen 104 from the proximal end 115.

Figure 5:
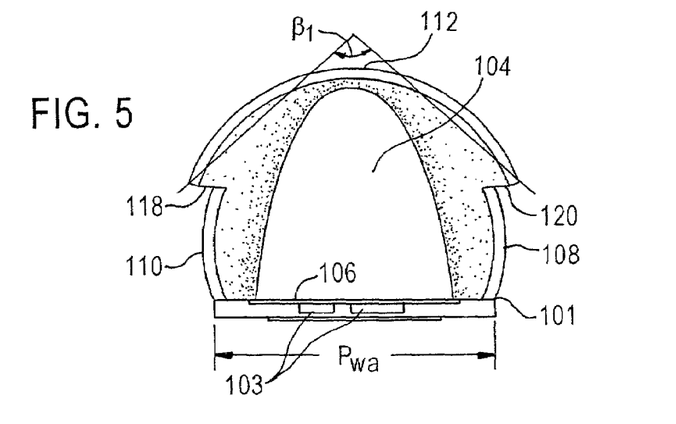
FIG. 5 is a transverse cross-section showing the proximal portion of the element shown in FIG. 1.
Figure 6:
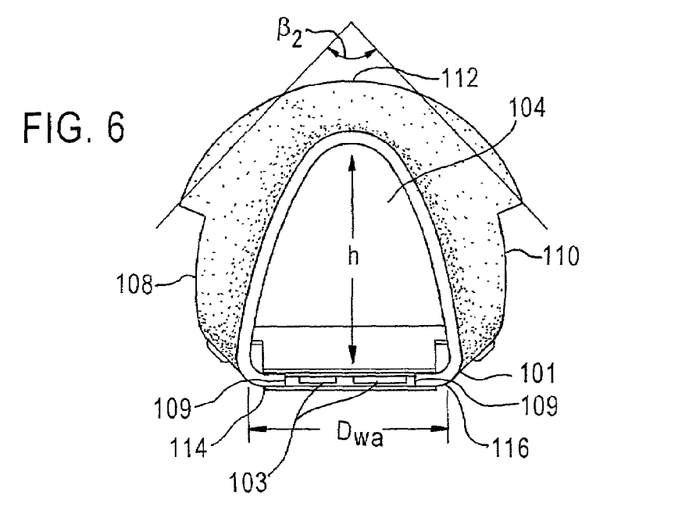
FIG. 6 is a transverse cross-section showing the distal portion of the element shown in FIG. 1.

As illustrated in FIGS. 5 and 6, each element 100A–C can further comprise at least one internal channel 103 disposed within the wall 101 that surrounds the lumen 104. In a phonomicrosurgical glottiscope, the base plate comprises internal channels 103, and the internal channels 103 are not limited as to a particular size or geometry or a particular function. For example, the internal channel 103 can be used for illumination, suction, or a laser fiber. In current aspects of the invention, however, the channel 103 allows proximate access to the distal end 113 of the element 100A–C. Furthermore, a tool or tools can be inserted into the channel 103 and these tools can access the distal end 113 of the element 100A–C. Therefore, an advantage of placing the channel 103 within the wall 101 surrounding the lumen 104 is that interference by the channel 103 to access of the lumen 104 is minimized.

The concept of placing tools within the internal channel 103 is not limited to a particular application. For example, tools can be placed in an internal channel 103 disposed in specula and examination tubes used in parts of the body such as the thorax, abdomen, pelvis, or joints. The internal channel 103 can also be positioned within the blade of a spatula laryngoscope, within a speculum blade such as those used to spread ribs during thoracic surgery, or, as described, used for a modular glottiscope or within a supraglottiscope of a type disclosed in U.S. Pat. No. 5,092,314 to Zeitels, and entitled Adjustable Supraglottiscope and Methods Therefor, which is incorporated herein by reference.

One or more tools can be used with the internal channels 103 of each element 100A–C, and this invention is not limited as to a particular configuration of tools/functions relative to each internal channel 103. For example, the tools can either be fixed to or detachable from the internal channel 103. Additionally, a single internal channel 103 can be used for more than one tool or function. For example, an internal channel 103 that provides illumination can also provide aspiration. Alternatively, multiple internal channels 103 can respectively be used for multiple tools/functions. In current aspects of the invention, however, separate internal channels 103 are used for separate tools/functions.

Figures 7A, 7B, 7C:
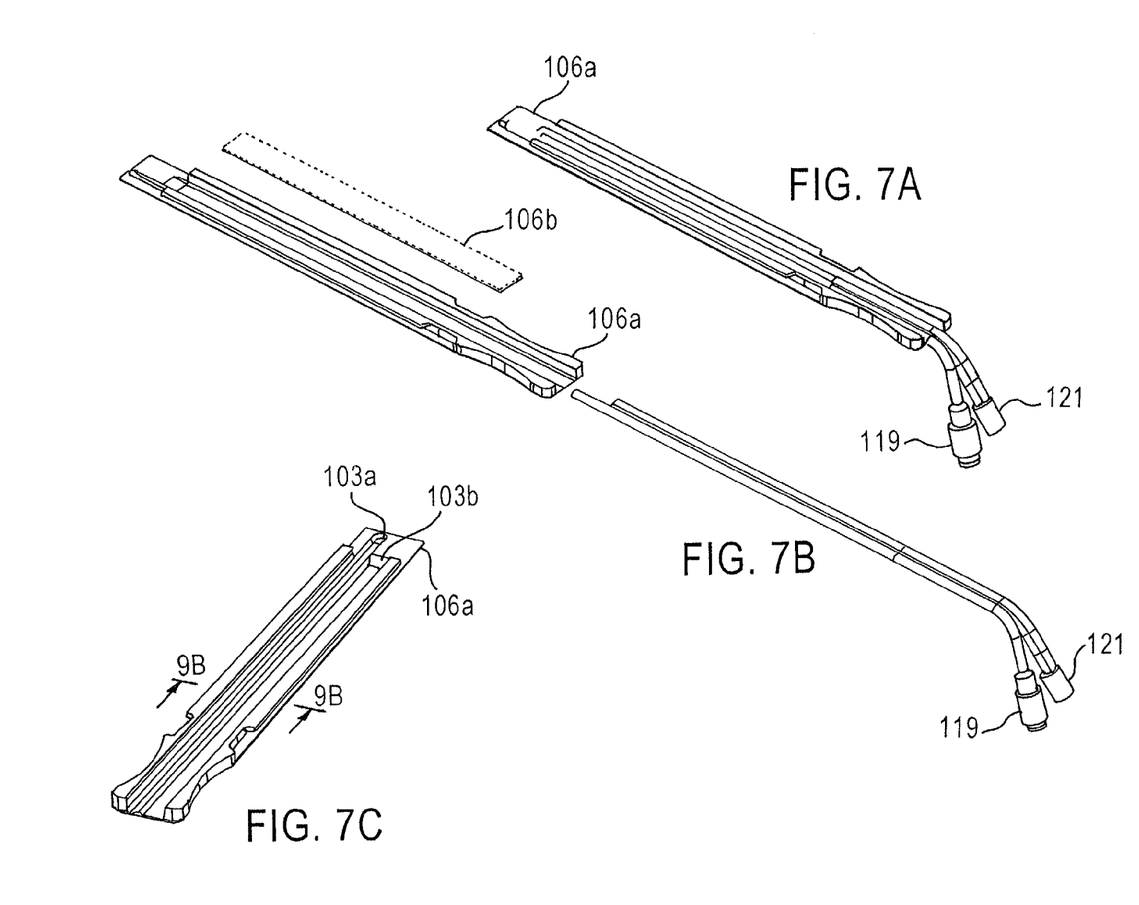
FIG. 7A is a perspective view of the bottom portion of a base plate with light and suction cannulae positioned in slots of the bottom portion.
FIG. 7B is an exploded of view of FIG. 7A showing the bottom portion of the base, two cannulas, and a top portion of the base.
FIG. 7C is a perspective view of the bottom portion of a base plate displaying internal slots but without the top portion, which creates the channels into the which two cannulae of FIG. 7B are positioned
Figure 8:
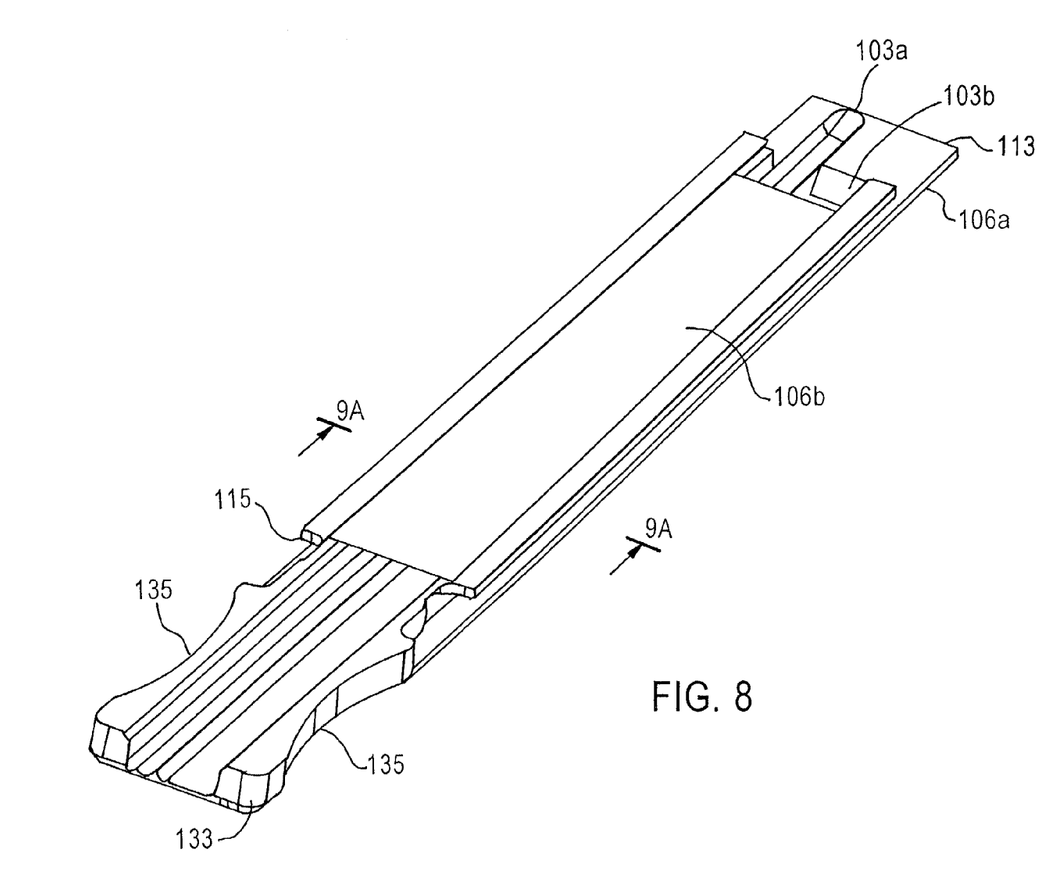
FIG. 8 is a perspective view of the top and bottom portions of the base plate of FIG. 7B.
Figure 9A:
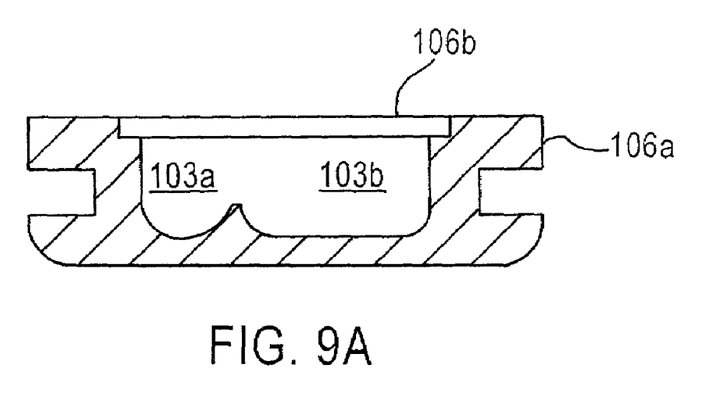
FIG. 9A is a cross section view of the base plate at line 9A—9A in FIG. 8.
Figure 9B:
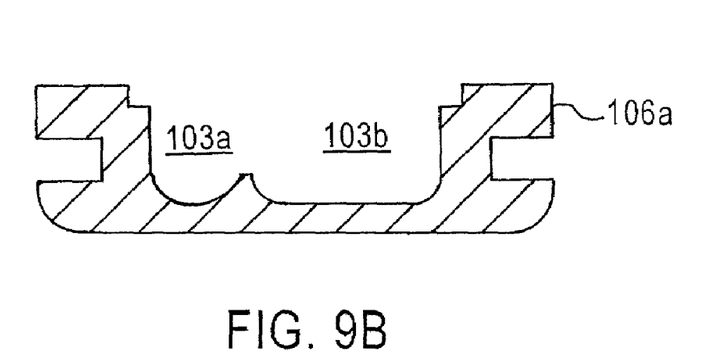
FIG. 9B is a cross section view of the base plate at line 9B—9B in FIG. 7C.

Referring to FIGS. 7–9, a first internal channel 103a is used for suction/aspiration of the distal end 113 and a second internal channel 103b is used to transmit illumination to the distal end 113. By providing illumination through the first internal channel 103b, the user of a modular glottiscope is able to transmit proximal lighting to the distal surgical field and thereby illuminate the vocal folds, and by providing aspiration through the second internal channel 103a, the user of the modular glottiscope is able to remove fluid, smoke, and/or other material from the surgical field. For example, tissue can be combusted and/or vaporized tissue resulting from the use of a laser can be removed. Other materials capable of being removed from the surgical field include mucosal secretions and blood. Although any devices capable of providing illumination and aspiration through the internal channels 103 is acceptable for use with invention, in current aspects of the invention, illumination and aspiration of the distal end 113 are respectively provided by a light cannula 119 and a suction cannula 121 having standard connecting joints for use with standard fiberoptic light cables and suction tubing.

The internal channels 103 can be positioned within any wall 101 of the element 100A–C. However, placing an internal channel 103 within a wall 101 typically requires that the wall 101 containing the internal channel 103 be thicker than normally would be required if the wall 101 did not have an internal channel 103. Furthermore, depending upon the particular use of the element 100A–C, certain portions of the element 100A–C cannot be easily widened without inhibiting the placement and advancement of the element 100A–C during use. A modular glottiscope is one example in which the placement of the internal channels 103 within the element 100A–C is limited, as the element 100A–C includes portions that cannot be easily widened, such as portions that engage the mandible, as well as the oral, pharyngeal, and supraglottal soft tissues.

In current aspects of the invention, in which the elements 100A–C are used to form a modular glottiscope system, the internal channels 103 are preferably positioned within a base 106. This position is advantageously least inhibiting because the base 106 is positioned, during use, adjacent to the maxilla, and the opening of the cavities of the mouth, pharynx, and supraglottis. The thickness or outer diameter of the base 106 can thereby be enlarged because enlargement of the base 106 is least likely to restrict placement and advancement in a patient with anatomical factors that inhibit placement of the glottiscope, such as narrow mandible, restricted tempomandibular joint opening, large tongue base, or elevated larynx.

Although the element 100A–C illustrated in FIGS. 1–4 is generally considered as being straight in the longitudinal direction, the invention is not limited in this manner. For example, the walls 101 of the element 100A–C can include an outward curve 125 at the distal end 113 (best shown in FIG. 13). This curved lip/tip 125 can be advantageous during laryngoscopic surgery for lifting the epiglottis, in particular for intubating instruments.

In current aspects of the invention, the elements 100A–C of a given set 100 are provided with a handle-attachment member 104 (best shown in FIG. 11) of a standard shape and size to permit easily attachment and detachment to a suitable handle (to be described later). Additionally, a pair of laterally opposed slots 118, 120, respectively formed in the curved sides 108, 100, can be provided at the proximal end 115 of each element 100A–C. The slots 118, 120 are preferably positioned beneath the handle attachment member 104 and adjacent the base 106. The height, "$S_{wa}$", of each of the slots 118, 120, is selected to permit movement therein of viewing and surgical operation tools, which the surgeon expects to use. The length, "$S_{1a}$", of the slots 118, 120 is likewise chosen to suit the surgeon's needs.

In current aspects of the invention, the base 106 is planar with a length, "$b_{1a}$," a proximal width, "$P_{wa}$" (FIG. 5) and a distal width, "$D_{wa}$" (FIG. 6). The base 106 is preferably smoothly contiguous with a pair of curved sides 108, 110 which intersect above at an apex line 112. The respective intersections between the curved sides 108, 110 at the apex line 112, of one curved side 108 with the planar base 106, and of the other curved side 110 with planar base 106, are all preferably formed to have smoothly rounded outside surfaces to avoid inflicting unnecessary trauma to the patient's tissues. Similarly, where the distal end opening 102 is defined by intersection of this complex triangular cross-section with an imaginary plane inclined at an angle "α" to the apex 112, the opening edge is also preferably smoothly rounded. A preferred range of α is 35°–90°. These features enable a surgeon to avoid inflicting unnecessary trauma on the patient's tissue as the distal end, with opening 102 therein, is inserted into a body cavity, for example, a patient's mouth and larynx during laryngoscopic surgery.

As is also readily seen from FIG. 5, the proximal end 115 of each element 100A–C, immediately above the laterally opposed slots 118, 120, generally has a D-shaped configuration with the form of a gently curved "inverted-U". Such a structure inherently possesses a degree of stiffness, which together with affixation to a preferably cylindrical handle-attachment member 104 (discussed below), provides sufficient rigidity and strength at the proximal end 115 to permit the transfer of significant forces which must be applied during surgery and treatment. Thus, the sizing and disposition of the slots 118, 120 to allow the residual portion of the element 100A–C to have an inverted "U" form for structural rigidity is deliberate and intended to ensure that the element 100A–C has sufficient inherent strength to perform its intended functions. The thickness of the walls 101 of the element 100A–C and the choice of material from which it is made are also taken into consideration regarding structural rigidity.

The element 100A–C is typically cleaned and sterilized, for subsequent reuse, after a particular surgical procedure. However, one-time disposable models could be used. Resterilization requires that the materials employed for the element 100A–C must be both tissue-compatible, i.e., capable of resisting any acidic substances (natural or medically applied), and capable of tolerating sterilization without adverse effect. There are numerous alloys and plastics available for such instruments, and stainless steel is a commonly preferred material. However, any known material capable of providing the required strength, tissue compatibility and sterilization-tolerance, is acceptable for use with this invention.

As mentioned earlier, a feature of the present system is that it has a high degree of modularity. This modularity is provided not only by selection of the dimensions for the elements 100A–C, but also on the curvatures, which includes the angle of intersection "$\beta_1$" between the curved sides 108, 110, as illustrated in FIG. 5. This angle is determined between the two planes respectively tangent to the curved sides 108, 110 at the apex line 112. Varying the height "h" for a given distal base width, "$D_{wa}$", and/or varying the curvature of each of the sides 108, 110, may result in a different angle, i.e., "$\beta_2$", at the intersection of the curved sides 108, 110 at the apex line 112 at the distal end 113 of the element 100A–C, as illustrated in FIG. 6. A preferred range of β is 30–150°. Varying the height "h" may also permit variation in the width of the opposed slots 118, 120, and thus the geometry of the space available to the surgeon to manipulate portions of surgical tools within the slots 118, 120. Likewise, different sizing may be accomplished at the proximal end 115. In general, the width, "$P_{wa}$", of the proximal end 115 of the base 106 can be greater than the width, "$D_{wa}$", of the distal end 113, so as to accommodate the surgeon's instruments. Also, as best shown in FIG. 8, the width of base 106 gradually decreases from the proximal end 115 to the distal end 113.

As persons skilled in the art of mechanical design will readily appreciate, the curvature of each of the sides 108, 110 need not be truly arcuate, namely sectors of a perfect circle. For example, during laryngoscopic surgery, because the normal human glottis has a particular shape, the sides 108, 110 may have different local radius of curvature at different points between the base 106 and the apex line 112. Also, portions of the sides 108, 110 close to the apex line 112 at the distal end may have a smaller radius of curvature than portions closer to the base 106. This can be reversed such that the sides 108, 110 can have a smaller local radius of curvature closer to the base 106 than closer to the apex line 112. The curvature of the upper part of the proximal end 115 may be similarly varied. These variations are mere matters of choice and the modularity of the present system readily accommodates such variations so that the surgeon may have the greatest flexibility to meet the needs of individual patients and surgical operations.

Although not necessary, in current aspects, the base 106 (FIGS. 2–4) is detachable from the element 100A–C. As discussed earlier, each element 100A–C is expected to be cleaned and sterilized after surgery, and a detachable base 106 allows easier access to both the base 106 and the element 100A–C. The detachability of the base 106 also allows for easier maintenance and repair of the base 106 and element 100A–C. Furthermore, the base 106 can be replaced with a new base 106, such as for repair, improvement or scheduled replacement, or a base 106 with one particular functionality can advantageously be swapped with a base 106 having a different functionality.

FIGS. 7–9 display a variety of views of the base plate. The invention is not limited as to a particular manner of attaching/detaching a base 106 to the element 100A–C. Many manners of attaching/detaching a base 106 to an element 100A–C are known, and any of these are acceptable for use with the invention. However, in current aspects, the base 106 has opposite recessed slots 109 that receive and mate with the corresponding inwardly extending ends of sides 108, 110, such that the base 106 can be separated from element 100A–C by sliding the base 106 rearward in the direction of the proximal end 115 of the element 100-C.

The base 106 may or may not include a slight lateral widening at the proximal end 115. When the base 106 is attached to the element by sliding the base 106 forward in the direction of the distal end 113, the base 106 engages the arch-shaped pair of opposing sides 108, 110 and elastically spreads the opposing sides 108, 110. The elastic force created by the opposing sides 108, 110 being spread creates a friction force that keeps the opposing sides 108, 110 and base 106 together. The lateral widening of the base plate can vary in thickness and length depending upon the amount of friction force that is desired and/or required to keep the opposing sides 108, 110 and base 106 together. The lateral widening of the base 106 is also partially determined by the thickness and rigidity of the opposing sides 108, 110.

In one aspect, the base 106 includes a proximal portion 133 with a down-slopping angle to accommodate the optical vectors of the surgical microscope. This angle may vary from to zero to forty-five degrees. In current aspects of the invention, the angle is about 10 degrees. The proximal portion 133 of the base 106 can also have bilateral concave radii 135 to serve as a place to manually hold the base 106 so that it can be removed from its attachment to the opposing sides 108, 110.

Many methods are known capable of forming internal channels 103 in a wall 101. The invention is not limited as to a particular method for forming the internal channels 103 within the wall 101 of the element 100A–C. For example, the wall 101 can be molded or cast with the internal channel 103 already present. Alternatively, the wall 101 can be molded or cast as a single piece with the internal channel 103 being subsequently formed within the wall 101. However, in a current aspect of the invention, the internal channel 103 is provided by forming a wall 101 with a slot in the wall 101 and then partially covering the slot with one or more additional pieces. The covered portion of the slot forms the internal channel 103.

This method advantageously allows greater access to the slot/channel 103 during manufacturing, which enables closer control of the geometry of the slot/channel 103. This greater access to the slot/channel 103 during manufacturing also allows a more complex geometry of the slot/channel 103 to be manufactured. Furthermore, greater accessibility to the slot/channel 103 advantageously also provides a user greater ability to change the functionality of each slot channel 103. Additionally, insertion and removal of tools and other objects into the slot/channel 103 is facilitated when the wall 101 and cover are disassembled and the slot is easily accessible.

Figure 10:
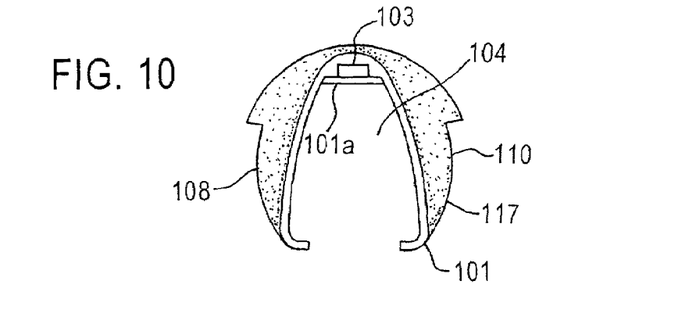
FIG. 10 is a transverse cross-section view of an element without the base plate and with a light cannula at the junction of the two arched walls of the examining speculum.

For the phonomicrosurgical aspect, as illustrated in FIGS. 5–9, in which channels 103 are formed in the base 106, the base 106 comprises a first portion 106a and a second portion 106b that are laminated together. The base 106 is preferably manufactured by milling a pair of longitudinally extending slots 103a, 103b within the first portion 106a. The thinner second portion 106b is then attached, for example by welding, to the top surface of the first portion 106a to cover the longitudinal slots 103a, 103b to thereby form the internal channels 103. This method allows for the introduction of cannulas for suction, lighting, or other instrumentation into the internal channels 103 when the first and second portions 106a, 106b are separated. The thickness of the lower portion of the base 106 may vary from about $30/1000$ inches to about $200/1000$ inches. In other aspects of the invention, for example, when the elements 100A–C are used for thoracic surgery, the thickness may be greater. As illustrated in FIG. 10, for the intubation aspect, the wall 101 includes a single slot, which is covered by an additional piece 101a to form an internal channel 103.

The size of the internal channels 103, in current aspects of the invention, are from $30/1000$ to $150/1000$ inches. However, the size of the internal channels 103 may be enlarged or reduced in width or depth depending upon the application for which the internal channel 103 will be used, for example for other types of instrumentation such as those used in spatulas for minimally invasive procedures in other portions of the body such as the chest and abdomen.

Figure 11:
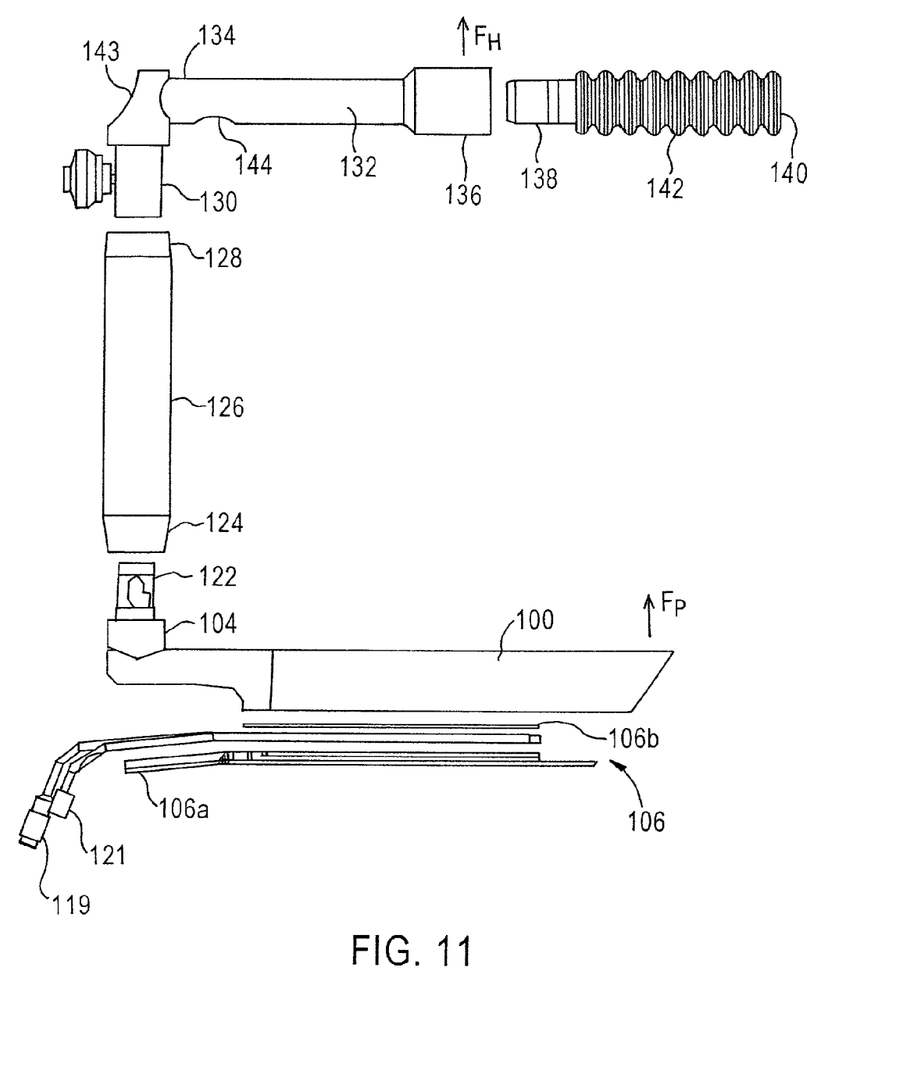
FIG. 11 is an exploded side view of a modular glottiscope system with the elements detached, and a handle and extension.
Figure 12:
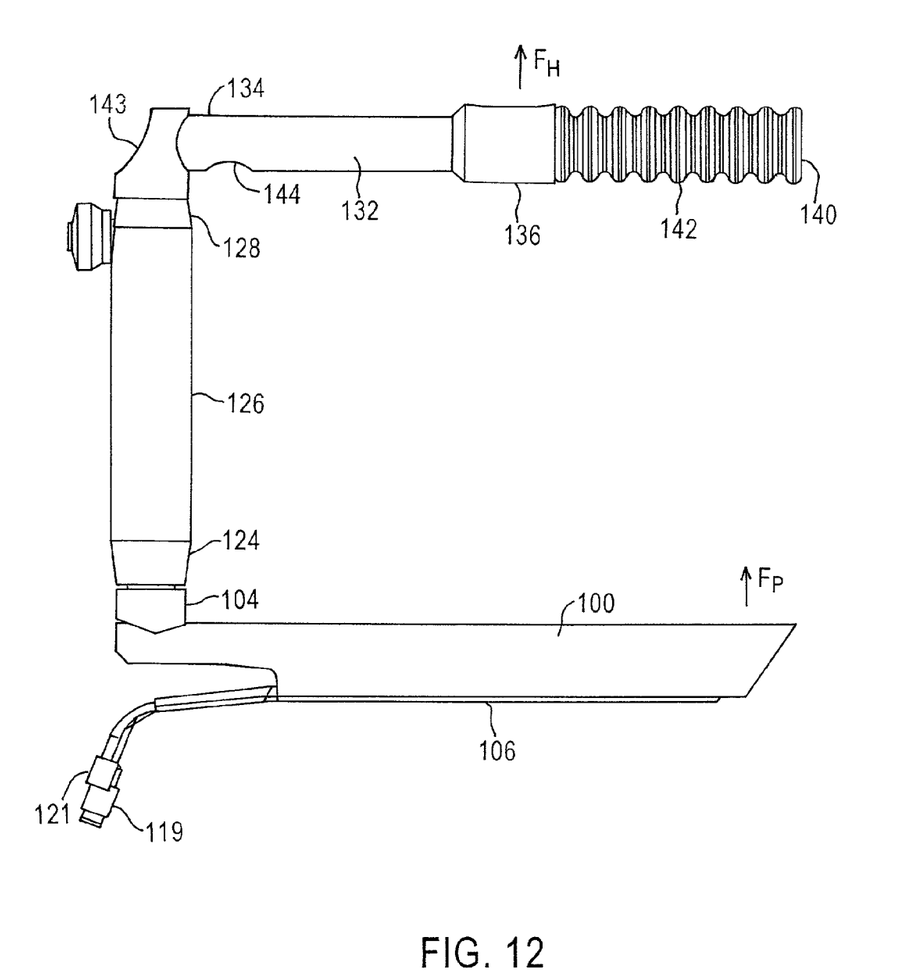
FIG. 12 is a side view of a modular glottiscope system with the elements attached.

FIGS. 11 and 12 are side views of certain basic components of a modular glottiscope system according to two aspects of the invention (phonomicrosurgical and orotracheal intubation). In this structure, which can be readily assembled, there is included a selected one of the elements 100A–C, as described above, now referred to as element 100. The handle-attachment member 104 may be readily made of the same material as the element 100 and may be welded, brazed, or otherwise affixed thereto. Over the distal end 122 of the handle-attachment member 104 may be fitted a lower end 124 of an elongate tubular extension element 126. One of the modular aspects of the present invention is that such extension elements 126 may be provided in a variety of lengths, although each should preferably have a standardized inside diameter selected to closely fit the standardized handle-attachment member 104. A short lateral connector part 130 of a generally "L" shaped handle 132 can also be inserted into the opposite end 128 of extension element 126. Some surgeons may prefer to have the extension element 126 to be other than a right cylindrical shape. For example, ergonomically suitable shapes for extension element 126 may be considered within the scope of this invention, such as having a central portion having an irregular and/or larger cross-sectional size while both end portions are in the form of circular right cylinders made smoothly contiguous with the central portion.

As shown in FIG. 11, the handle 132 has a first end 134 which may be closed off and be perpendicular to the longitudinal direction. The handle 132 can also include a distal end opening 136 into which an end 138 of a handle extender element 140 can be inserted. Also, the handle extender element 140 can be provided with an outer flexible cover having easy-to-grip ridges 142. The structure, hitherto referred to as the handle 132, may be considered an intermediate element between the handle extender 140 and the extension element 126.

The handle 132 can include a smoothly curved corner surface 143 to provide an ergonomic rest for the surgeon's thumb of the hand holding extension element 126 during manipulation of the glottiscope. Thus, a surgeon grasping the handle portion 132 or the handle extender 140 with one hand may grasp extension element 126 with the other hand while resting the thumb of that particular hand on the curved recess surface 143 for comfort and convenience.

In current aspects of the invention, the extension element 126 is securely fittable to the handle-attachment member 104, the connector part 130 of handle 132 is securely fittable to the opposite end 128 of the extension element 126, and the end 138 of the handle extender 140 is securely fittable to the end 136 of the handle portion 132. For reasons of scale, FIG. 11 does not show the minor details of how such a mechanism would appear as persons of ordinary skill in the art will be aware of and be able to adapt any of numerous known structures and techniques for providing such secure but readily detachable attachments. Examples of such detachably attachable mechanisms include bayonet fittings, and other generally available systems known for the same general purpose. The exact nature and form of such mechanisms is not critical to the present invention. All that is required is that various attachments be capable of easy and secure attachment and ready detachment as necessary for separate and effective sterilization of the various parts.

To facilitate the surgeon's activity, in one aspect of the invention, the extension element 126, handle portions 132 and 130, as well as handle extender 140 are formed from strong but relatively lightweight materials. Numerous alloys, composites, and other materials are known to persons of ordinary skill in the art, and any of these materials may be selected as desired. The exact choice of materials is not considered critical for this invention, although it is preferred that the entire structure be relatively light. The surgeon may be expected to attach either the handle portion 132 or the handle extender 140, in any known manner, to an external suspension system and to manipulate the same to apply significant forces to the patient against the pull of gravity.

Known external suspension and fulcrum-holder systems for such equipment include, but are not necessarily limited to, the Boston University Suspension System, the Loeb Laryngoscope Holder Support, and other "gallows"-type systems known in the art. These systems may require the addition of appropriately formed known elements to the components described hitherto. Such obvious modifications are considered well within the knowledge of persons of ordinary skill in the art, various elements of such systems are well-known and commercially available, and a detailed description thereof is therefore believed to be unnecessary and is omitted for conciseness.

As indicated in FIGS. 11 and 12 arrows identified as "$F_H$" and "$F_P$", where a force "$F_H$" is applied by the surgeon via the handle structure, with element 100 inserted into a patient's larynx, a consequential force "$F_P$" will be exerted on the patient. These forces can be significant, and a principal reason for choosing the depicted cross-section for element 100, with curved sides coming together at a smoothly curved apex line, is to facilitate the application of such a force in a manner most advantageous for the surgeon without inflicting unnecessary trauma on the patient's tissues. Persons of ordinary skill in the art of performing laryngoscopic procedures will understand exactly how such forces are applied and why they are necessary to provide appropriate access to tissue to be treated.

Figure 13:
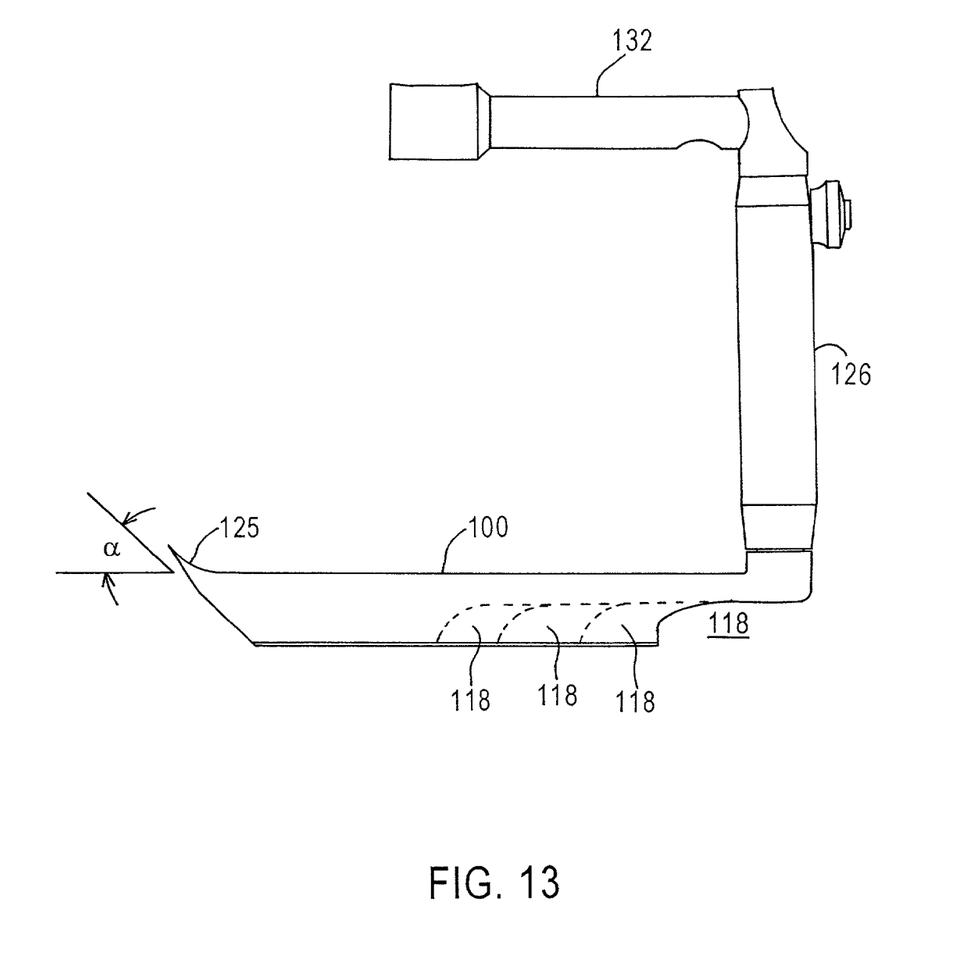
FIG. 13 is a side view of a modular glottiscope system in which the element includes a distal curved lip.

An alternative aspect of the invention is illustrated in FIGS. 10 and 13, in which the arch-shaped upper portion 117 of the element 100 may be used without a base as a specially-designed intubation variation. An intubation modular glottiscope system comprises an examining spatulae with a lancet-arch-shaped distal element with or without a curved distal lip to lift the epiglottis. This distal shape conforms to the glottal aperture and precludes edematous or neoplastic laryngeal tissue from obstructing the view of the glottal aperture thereby ensuring for effective endotracheal tube placement.

In this aspect of the invention in which there may be a lateral slot 118 of variable length, the arch shape of the upper portion 117 provides a direct path to the glottal aperture and precludes soft tissue of the larynx, pharynx or oral cavity from obscuring visualization of the glottal aperture, which can complicate orotracheal intubation. Also, an internal channel 103 to provide illumination can be placed at the intersection of the sidewalls 108, 110 adjacent the top of the lumen 104 of the element 100. Placement of the light carrier in this location is ideal for intubation because visualization of the posterior glottis (interarytenoid region) is necessary, but visualization of the anterior glottal commissure is not. The distal arch-shaped element 100 without a base is distinctly different from various standard intubation spatula blades. The proximal lateral slot 118 facilitates introduction of the endotracheal tube. Additionally, this aspect of the element 100 may be much narrower because only a monocular view is necessary for intubation, and the wide proximal aperture used for micro-laryngoscopy and instrumental tissue retraction is not needed. Also, angle α can be much more acute or the element 100 can have a distal curved lip 125 to facilitate lifting the epiglottis for enhanced visualization of the laryngeal introitus.

The handle extender 140, described above with relation to FIG. 11, is omitted, and the extension element 126 may be used alone with the element 100 giving the assembled instrument a generally L-shape. Alternatively, the handle 132, the extension element 126, and the element 100 can be used, giving the instrument a generally C-shape. The extension element 126 and the handle 132 may also be designed to retrofit standard anesthesia intubating spatula blades. Additionally, the handle 132 may be designed to attach to standard anesthesia "L" shaped intubation laryngoscopes.

The clinician may choose to use the phonomicrosurgical glottiscope for intubation rather than the standard orotracheal intubation model in selected circumstances such as an upper airway emergency created be a large obstructing tumor of the larynx or pharynx. The surgeon introduces an anesthetic-delivery endotracheal tube longitudinally through the laryngoscope element 100 and out of the end opening 102, through the vocal fold aperture and into the patient's trachea. Once accomplished, the planar base can be detached so that the upper portion 117 of the glottiscope can be removed from the patient's throat without disturbing the endotracheal tube. Subsequently, an anesthetic substance, by itself or mixed with other substances, can be administered at a controlled rate for as long as needed. Similar intubation may be employed to suck out liquids from a patient's lungs through the trachea.

When the system is to be employed for laryngoscopic/glottiscopic procedures, the element 100 will be positioned in the larynx of a conveniently disposed patient with the outer surface of the base part of the element cross-section immediately adjacent the patient's upper mandible. This will ensure that the apex line is immediately adjacent the lower mandible of the patient, and this is particularly suitable, with appropriate choice of dimensions of the element 100, for applying the distal end 113 to the laryngeal tissue in the most advantageous manner.

The present invention can be practiced by employing conventional materials, methodology and equipment. Accordingly, the details of such materials, equipment and methodology are not set forth herein in detail. In the previous descriptions, numerous specific details are set forth, such as specific materials, structures, chemicals, processes, etc., in order to provide a thorough understanding of the present invention. However, it should be recognized that the present invention can be practiced without resorting to the details specifically set forth. In other instances, well known processing structures have not been described in detail, in order not to unnecessarily obscure the present invention.

Only the preferred embodiment of the present invention and but a few examples of its versatility are shown and described in the present disclosure. It is to be understood that the present invention is capable of use in various other combinations and environments and is capable of changes or modifications within the scope of the inventive concept as expressed herein.

What is claimed is:

1. An element for a surgical laryngoscope speculum system, comprising:
   a proximal end;
   a distal end;
   at least one wall defining a lumen extending from said proximal end to said distal end, the at least one wall including a substantially planar base; and
   at least one internal channel disposed within said at least one wall, wherein
   in cross-section perpendicular to a longitudinal axis of the lumen, an entire inner surface of the at least one wall facing the lumen has substantially the same shape as an entire outer surface of the at least one wall,
said distal end is adapted for insertion into a body cavity,
said at least one wall defines a distal opening to a first of said at least one internal channel, said distal opening adjacent said distal end, and
tools may be inserted operatively into said lumen from said proximal end.

2. An element according to claim 1, wherein the base having a first channel for providing illumination to said distal end and a second channel for providing aspiration to said distal end.

3. An element according to claim 1, wherein said at least one wall further includes a pair of opposing curved sides intersecting at a predetermined first angle at an apex line.

4. An element according to claim 3, wherein the base having a thickness greater than a thickness of said curved sides.

5. An element according to claim 3, wherein said first angle is between about 30° and about 150°.

6. An element according to claim 1, wherein the a base having a first portion and a second portion, said first portion having at least one slot, said second portion covering each said at least one slot respectively forms each said at least one internal channel.

7. An element according to claim 1, wherein a proximal portion of said base has a down-sloping angle between about 0° and about 45°.

8. An element according to claim 1, wherein said at least one wall defines a proximal opening to said first internal channel, said proximal opening adjacent said proximal end.

9. An element according to claim 1, wherein said at least one wall includes a pair of opposing curved sides.

10. An element according to claim 9, wherein one of said at least one internal channel for providing illumination to said distal end is disposed at an intersection of said opposing curved sides.

11. An element according to claim 10, wherein said curved sides each include longitudinally extending free ends which define an opening to said lumen.

12. An element according to claim 1, wherein the element includes a curved distal lip.

13. An element according to claim 1, wherein said at least one wall includes an arch-shaped portion having lateral slots, the base inserted into the lateral slots of the arch-shaped portion, and the being wider than the lumen.

14. An element according to claim 1, wherein said distal end is lancet-arch-shaped, wherein the distal end conforms to a glottal aperture and prevents edematous or neoplastic laryngeal tissue from obstructing a view of the glottal aperture.

15. An element according to claim 14, wherein the element includes a curved distal lip.

16. An element for a surgical laryngoscope speculum system, comprising:
a proximal end;
a distal end;
at least one longitudinally extending wall defining a lumen extending from said proximal end to said distal end, said at least one wall including
a substantially planar base, and
a pair of opposing curved sides intersecting at a predetermined first angle at an apex line; and
at least one internal channel disposed within the base, wherein
said distal end is adapted for insertion into a body cavity,
tools may be inserted operatively into said lumen from said proximal end,
said distal end has a generally triangular cross-section defined by said base and said pair of curved sides, and
said cross-section intersecting at a predetermined second angle with said base.

17. An element according to claim 16, wherein said second angle is between about 35° and about 90°.

18. An element for a surgical laryngoscope speculum system, comprising:
a proximal end;
a distal end;
at least one longitudinally extending wall defining a lumen extending from said proximal end to said distal end, said at least one wall including
a substantially planar base, and
a pair of opposing curved sides intersecting at a predetermined first angle at an apex line; and
at least one internal channel disposed within the base, wherein
said distal end is adapted for insertion into a body cavity,
tools may be inserted operatively into said lumen from said proximal end, and
said base is detachably connected to said curved sides.

19. An element for a surgical laryngoscope speculum system, comprising:
a proximal end;
a distal end;
at least one longitudinally extending wall defining a lumen extending from said proximal end to said distal end, said at least one wall including a substantially planar base, a proximal portion of said base has a down-sloping angle between about 0° and about 45°; and
at least one internal channel disposed within the at least one wall, wherein
said distal end is adapted for insertion into a body cavity,
tools may be inserted operatively into said lumen from said proximal end, and
said proximal portion of said base includes a pair of bilateral concave radii.

20. An element for a modular surgical laryngoscope speculum system, comprising:
a proximal end;
a distal end;
a pair of opposing curved sides;
a substantially planar base removably attached to said pair of curved sides, said base and said curved sides defining a lumen extending from said proximal end to said distal end;
a first internal channel disposed within said base for providing illumination to said distal end; and
a second internal channel disposed within said base for providing aspiration to said distal end, whereby said distal end is for insertion into a body cavity and tools may be inserted operatively into said lumen from said proximal end.

21. A modular surgical laryngoscope speculum system, comprising:
a plurality of elements of respectively different counterpart dimensions, each said elements having a proximal end, a distal end, a pair of opposing curved sides, a base removably attached to said pair of curved sides, and at least one channel disposed within said base, wherein said base and said curved sides define a lumen extending from said proximal end to said distal end, whereby said distal end is for insertion into a body cavity and tools may be inserted operatively into said lumen from said proximal end;

a standardized handle-attachment member affixed adjacent said proximal end of each of said plurality of elements; and a handle attachable to said standardized handle-attachment member of any of said elements.

22. A modular surgical laryngoscope speculum system according to claim 21, wherein said base includes a first channel for providing illumination to said distal end and a second channel for providing aspiration to said distal end.

* * * * *